United States Patent [19]

Zimmerman et al.

[11] Patent Number: 5,425,940
[45] Date of Patent: * Jun. 20, 1995

[54] COMBINATION THERAPY USING INTERLEUKIN-2 AND TUMOR NECROSIS FACTOR

[75] Inventors: Robert Zimmerman, Lafayette; Jeffrey L. Winkelhake, Emeryville, both of Calif.

[73] Assignee: Cetus Oncology Corporation, Emeryville, Calif.

[*] Notice: The portion of the term of this patent subsequent to Sep. 5, 2006 has been disclaimed.

[21] Appl. No.: 191,277

[22] Filed: Feb. 3, 1994

Related U.S. Application Data

[60] Continuation of Ser. No. 743,075, Aug. 9, 1991, abandoned, which is a division of Ser. No. 371,203, Jun. 26, 1989, Pat. No. 5,098,702, which is a division of Ser. No. 273,760, Nov. 16, 1988, Pat. No. 4,863,727, which is a continuation of Ser. No. 80,493, Jul. 31, 1987, abandoned, which is a continuation-in-part of Ser. No. 943,608, Dec. 18, 1986, abandoned, which is a continuation-in-part of Ser. No. 884,548, Jul. 11, 1986, abandoned, which is a continuation-in-part of Ser. No. 849,713, Apr. 9, 1986, abandoned.

[51] Int. Cl.⁶ .................... A61K 45/05; A61K 37/02
[52] U.S. Cl. .................... 424/85.1; 424/85.2; 514/2; 514/8
[58] Field of Search .................... 424/85.1, 85.2; 514/2, 514/8

[56] References Cited

U.S. PATENT DOCUMENTS

| | | | |
|---|---|---|---|
| 4,401,756 | 8/1983 | Gillis | 435/68 |
| 4,447,355 | 5/1984 | Sakamoto et al. | 424/85.2 |
| 4,518,584 | 5/1985 | Mark et al. | 424/85.2 |
| 4,530,787 | 7/1985 | Shaked et al. | 260/112 R |
| 4,569,790 | 2/1986 | Koths et al. | 260/112 R |
| 4,572,798 | 2/1986 | Koths et al. | 260/112 R |
| 4,588,585 | 5/1986 | Mark et al. | 424/85 |
| 4,604,377 | 8/1986 | Fernandes et al. | 514/8 |
| 4,650,674 | 3/1987 | Aggarwal et al. | 424/85 |
| 4,677,063 | 6/1987 | Mark et al. | 435/68 |
| 4,677,064 | 6/1987 | Mark et al. | 435/68 |
| 4,766,106 | 8/1988 | Katre et al. | 514/12 |
| 4,863,726 | 9/1989 | Stevens et al. | 424/85.2 |
| 4,863,727 | 9/1989 | Zimmerman et al. | 424/85.2 |
| 4,917,888 | 4/1990 | Katre et al. | 424/85.91 |
| 5,066,584 | 11/1991 | Gyllensten et al. | 435/91 |
| 5,098,702 | 3/1992 | Zimmerman et al. | 424/85.2 |
| 5,206,344 | 4/1993 | Katre et al. | 530/351 |

FOREIGN PATENT DOCUMENTS

| | | |
|---|---|---|
| 28033 | 5/1981 | European Pat. Off. . |
| 88195 | 9/1983 | European Pat. Off. . |
| 91539 | 10/1983 | European Pat. Off. . |
| 107498 | 5/1984 | European Pat. Off. . |
| 131789 | 1/1985 | European Pat. Off. . |
| 146026 | 6/1985 | European Pat. Off. . |

(List continued on next page.)

OTHER PUBLICATIONS

Borden, "Interferons: Rationale for Clinical Trials in Neoplastic Disease," *Ann. Intern. Med.*, 91:472–479 (1979).

(List continued on next page.)

*Primary Examiner*—Jacqueline Stone
*Attorney, Agent, or Firm*—David A. Gass; Philip L. McGarrigle; Robert P. Blackburn

[57] ABSTRACT

Anti-tumor activity in mammals can be augmented by administering to the mammalian host a synergistically effective amount of TNF and IL-2 or of TNF and IFN-$\beta$, or of TNF, IL-2 and IFN-$\beta$ in combination. The composition of TNF and IL-2 and/or IFN-$\beta$ may be prepared in vitro or administered separately to the host. If the TNF and IL-2 are administered sequentially, the TNF must be administered prior to the IL-2 to obtain synergy. The composition is useful for treating such cancers as mastocytoma, melanoma, leukemia, lymphoma, mammary adenocarcinoma, and pharyngeal squamous cell carcinoma.

24 Claims, No Drawings

FOREIGN PATENT DOCUMENTS

| | | |
|---|---|---|
| 148311 | 7/1985 | European Pat. Off. . |
| 149551 | 7/1985 | European Pat. Off. . |
| 155549 | 9/1985 | European Pat. Off. . |
| 158286 | 10/1985 | European Pat. Off. . |
| 168214 | 1/1986 | European Pat. Off. . |
| 170843 | 2/1986 | European Pat. Off. . |
| 3411184 | 10/1985 | Germany . |
| 2063882 | 6/1981 | United Kingdom . |
| 2158829 | 11/1985 | United Kingdom . |
| WO86/02381 | 4/1986 | WIPO . |

OTHER PUBLICATIONS

Buessow et al., "Tumoricidal Activity of an Acute Promyelocytic Leukemis Cell Line (HL-60) is Augmented by Hyman Inteferon Alpha," *Leukemia Res.*, 8:801–811 (1984).

Carswell et al., "An endotoxin-induced serum factor that causes necrosis of tumors", *PNAS (USA)*, 72:3666–3670 (Sep., 1975).

DeClercq et al., "Synergism in the Antitumor Effects of Type 1 and Type II Interferon in Mice Inoculated With Leukemia L1210 Cells," *Cancer Letters*, 15:223–228 (1982).

Dempsey et al., "The Differential Effects of Human Leukocytic Pyrogen/Lymphocyte-Activating Factor, T Cell Growth Factor, and Interferon on Human Natural Killer Activity", *J. Immunol.*, 129:2504 (Dec. 1982).

Devos et al., "Molecular Cloning of Human Interleukin 2 cDNA and its Expression in *E. coli*", *Nucl. Acids Res.*, 11:4307 (1983).

Fleishman, "Potentiation of the Direct Anticellular Activity of Mouse Interferons: Mutal Synergism and Interferon Concentration Dependence", *Cancer Res.*, 42:869–875 (Mar. 1982).

Gray et al., "Cloning and expression of cDNA for human lymphotoxin, a lymphokine with tumour necrosis activity", *Nature*, 312:721 (Dec. 1984).

Haranaka et al., "Antitumor Activity of Murine Tumor Necrosis Factor (TNF) Against Transplanted Murine Tumors and Heterotransplanted Human Tumors in Nude Mice", *Int. J. Cancer*, 34:263 (1984).

Haranaka et al., "Cytotoxic Activity of Tumor Necrosis Factor (TNF) on Human Cancer Cells in vitro," *Jap. J. Exp. Med.*, 51:191–194 (1981).

Lopez-Botet et al., "Interleukin 2 and interferon-γ are not sufficient to induce natural killer-like activity in human T cell clones," *Eur. J. Immuno.*, 14:1137–1141 (1984).

Matsunaga et al., "Augmentation of In Vitro Cytotoxicity and In Vivo Tumor-Inhibition by Combined Use of Lymphotoxin-Containing Supernatants and Antitumor Drugs", *Cancer Letters*, 20:21 (1983).

Matthews et al., "Tumor-Necrosis Factor from the Rabbit. III. Relationship to Interferons," *Chem. Abstr.*, 92:108513h (1980).

Metz, "Interferon and Interferon Inducers," *Adv. Drug Res.*, 10:101–156 (1975).

Morgan et al., "Selective in vitro Growth of T Lymphocytes from Normal Human Bone Marrows," *Science*, 193:1007–1008 (Sep. 1976).

Mule et al., "Adoptive Immunotherapy of Established Pulmonary, Metastass with LAK Cells and Recombinatn Interleukin-2," *Science*, 225:1487–1489 (Sep. 1984).

Papermaster et al., "Lymphokine Adjuvant Therapy: Bioassay of Human Lymphokine Fractions in a Mouse Tumor Model", *Hum. Lymphokines;* Khan et al., (ed), pp. 459–477 (Jun. 30, 1982).

Paucker et al., "Quantitative Studies on Viral Interference in Suspended L Cells III. Effect of interfering Viruses and Interferon on the Growth Rate of Cells," *Virology*, 17:324 (1962).

Pennica et al., "Human tumour necrosis factor: precursor structure, expression and homology to lymphotoxin", *Nature*, 312:724 (Dec. 1984).

Rosenberg et al., "Observations on the Systemic Ad- (List continued on next page.)

OTHER PUBLICATIONS ministrtion of Autologous Lymphokine-Activated Killer Cells and Recombinant Interleukin-2 to Patients with Metastatic Cancer", *N. Eng. J. Med.,* 313:1485 (Dec. 1985).

Rosenberg et al., "A New Approach to the Adoptive Immunotherapy of Cancer with Tumor-Infiltrating Lymphocytes", *Science,* 233:1318 (Sep. 1986).

Sande et al., "Antimicrobial Agents," in the Pharmacological Basis of Therapeutics, Goodman et al., (eds.), MacMillan Publishing: N.Y., pp. 1080-1105 (1980).

Shalaby et al., "In Vivo Augmentation of Natural Killer Activity by Combined Treatment with Recombinant Gamma Interferon and Interleukin-2", *J. Inteferon Res.,* 5:571 (1985).

Shirai et al., "Cloning and expression in *Escherichia coli* of the gene for human tumour necrosis factors", *Nature,* 313:803 (Feb. 1985).

Svedersky et al., "Augmenttion of Human Natural Cell-Mediated Cytotoxicity by Recombinant Human Interleukin 2", *J. Immunol.,* 133:714 (Aug. 1984).

Taniguchi et al., "Structure and expression of a cloned cDNA for human interleukin-2", *Nature,* 302:305 (Mar. 1983).

Wang et al., "Site-Specific Mutagenesis of the Human Interleukin-2 Gene: Structure-Function Analysis of the Cysteine Residues", *Science,* 224:1431 (Jun. 1984).

Wang et al., "Molecular Cloning of the Complementary DNA for Human Tumor Necrosis Factor," *Science,* 228:149-154 (Apr. 1985).

Williams et al., "In vitro Synergism between Inteferons and Human Lymphotoxin: Enhancement of Lymphotoxin-Induced Target Cell Killing", *J. Immunol.,* 130:518 (Feb. 1983).

Williamson et al., "Human tumor necrosis factor produced by human B-cell lines: Synergistic cytotoxic interaction with human interferon", *PNAS (USA),* 80:5397 (Sep. 1983).

Winkelhake et al., "Immunological Block to Synthetic α-Melanocyte-stimulating Hormone: Melanocyte Interaction by Antibodies Isolated from Cell-Column Immunoadsorbents", *Cancer Res.,* 39:3058-3064 (Aug. 1979).

COMBINATION THERAPY USING INTERLEUKIN-2 AND TUMOR NECROSIS FACTOR

This is a continuation of U.S. patent application Ser. No. 07/743,075, filed Aug. 9, 1991, abandoned as of the filing date granted this application; in turn a divisional of Ser. No. 371,203 filed Jun. 26, 1989, now U.S. Pat. No. 5,098,702 issued Mar. 24, 1992, which is a divisional of Ser. No. 273,760, filed Nov. 16, 1988 which issued Sep. 5, 1989 as U.S. Pat. No. 4,863,727, which is a continuation of U.S. Ser. No. 80,493, filed Jul. 31, 1987, abandoned, which is a continuation-in-part of Ser. No. 943,608, filed Dec. 18, 1986, abandoned, which is a continuation-in-part of Ser. No. 884,548, filed Jul. 11, 1986, abandoned which is a continuation-in-part of Ser. No. 849,713, filed Apr. 9, 1986, abandoned.

BACKGROUND OF THE INVENTION

This invention relates to a combination of interleukin-2 (IL-2) and/or interferon-$\beta$ (IFN-$\beta$) and tumor necrosis factor (TNF) and the use of this combination as an anti-tumor therapeutic agent.

IL-2, a lymphokine which is produced by normal peripheral blood lymphocytes and induces proliferation of antigen or mitogen stimulated T cells after exposure to plant lectins, antigens, or other stimuli, was first described by Morgan, D. A., et at., *Science* (1976), 193:1007–1008. It is now recognized that in addition to the growth factor properties of IL-2, IL-2 modulates a variety of functions of immune system cells in vitro and in vivo.

IL-2 was initially made by cultivating human peripheral blood lymphocytes (PBL) or other IL-2-producing cell lines. See, for example, U.S. Pat. No. 4,401,756. Recombinant DNA technology has provided an alternative to PBLs and cell lines for producing IL-2. Taniguchi, T. et al., *Nature* (1983), 302:305–310 and Devos, R., *Nucleic Acids Research* (1983), 11:4307–4323 have reported cloning the human IL-2 gene and expressing it in microogranisms.

U.S. Pat. No. 4,518,584 describes and claims muteins of IL-2 in which the cysteine normally occurring at position 125 of the wild-type or native molecule has been replaced with a neutral amino acid, such as serine or alanine. Copending U.S. application Ser. No. 06/810,656 filed Dec. 17, 1985 discloses and claims an oxidation-resistant mutein such as IL-2 which is biologically active wherein each methionine residue of the protein from which the mutein is derived which methionine is susceptible to chloramine T or peroxide oxidation is replaced with a conservative amino acid such as alanine. These IL-2 muteins possess the biological activity of native IL-2. U.S. Pat. Nos. 4,530,787 and 4,569,790 disclose and claim methods for purifying recombinant native IL-2 and muteins thereof, as well as the purified form of IL-2.

U.S. Pat. No. 4,604,377 discloses an IL-2 composition suitable for reconstituting in a pharmaceutically acceptable aqueous vehicle composed of oxidized microbially produced recombinant IL-2. The IL-2 is noted as useful in combination with cytotoxic chemotherapy or irradiation or surgery in the treatment of malignant or premalignant diseases in a direct therapeutic or adjuvant setting or in combination with other immune-modulating drugs, lymphokines (e.g., IL-1, IL-3, CSF-1 and IFNs) naturally occurring or inducible anti-cellular toxins in treating malignant diseases.

Various therapeutic applications of human IL-2 have been investigated and reported by S. Rosenberg and colleagues (see Mule et al., *Science* (1984), 225:1487 and S. Rosenberg et al., *New England Journal of Medicine* (1985), 313:1485–1492, for example).

Interferons (IFN) constitute a group of naturally occurring proteins that are known to exhibit anti-viral, anti-tumor and immunoregulatory behavior. Two types of IFN have been identified based on differences in their observed biological properties and molecular structures: Type I and Type II. Beta-interferon (IFN-$\beta$) is a Type I IFN that can be induced in fibroblasts by viral challenge and contains about 165 amino acids. IFN-$\alpha$ is also a Type I IFN inducible in leukocytes, and IFN-$\gamma$ is a Type II IFN that is induced in lymphocytes in response to specific mitogenic stimuli and contains 146 amino acids.

Human IFN-$\beta$ may be produced by recombinant DNA technology, as described, for example, in EP 28,033 published Jun. 6, 1981 to Sugano, et al. and U.K. 2,063,882 published Jun. 10, 1981 to Revel, et al. Additionally, the IFN-$\beta$ may be a mutein in which amino acids not essential to biological activity are deleted or replaced with other amino acids to increase stability, as described by U.S. Pat. No. 4,588,585, the disclosure of which is incorporated herein by reference. Mouse IFN-$\beta$ may also be produced by recombinant DNA technology.

After Paucker et al., *Virology*, 17:324–334 (1962) showed that IFN suppressed the growth rate of mouse L cells, many investigators have studied treatment of mouse L cells with IFN and inhibition of tumor cell proliferation by IFN. See, e.g., Borden, E. C., *Ann. Intern. Med.*, 91:472–479 (1979).

Tumor necrosis factor (TNF) was first described by Carswell et al., PNAS (U.S.A.) (1975), 72:3666–3670 as an endotoxin-induced serum factor which causes necrosis of chemically transformed tumor cells when growing in mice. Purified preparations of murine TNF have been tested against murine and human cell lines in vitro. K. Haranaka and N. Satomi, *Japan J. Exp. Med.* (1981), 51:191. In contrast to normal cells, tumor cell lines from both species were susceptible to the cytotoxic activity of the mouse TNF. Furthermore, the murine TNF was reported to be toxic against both human- and mouse-transplanted tumors in nude mice. See K. Haranaka et al., *Int. J. Cancer* (1984), 34:263–267. Human TNF is also known to be cytotoxic to neoplastic cells, and has been produced in recombinant form. See Pennica et al., Nature (1984), 312:724–729; Shirai et al., *Nature* (1985), 313:803–806; Wang et al., *Science* (1985), 228:149–154.

The cloning of rabbit TNF is disclosed in EP 146,026, published Jun. 26, 1985 (Dainippon PHarmaceutical Co., Ltd.) and EP 148,311, published Jul. 17, 1985 (Asahi Kasei Kogyo Kabushiki). The cloning of human TNF having 151 and 155 amino acids (2 and 6 less than the native form) is disclosed in EP 155,549, published Sep. 25, 1985 (Dainippon Pharmaceutical Co., Ltd.), and human TNF having 155 amino acids is disclosed in EP 158,286, published Oct. 16, 1985 (Asahi Kasei Kogyo Kabushiki Kaisha) and corresponding GB 2,158,829A, published Nov. 20, 1985. The cloning of mature TNF (157 amino acids) and various modified forms (muteins) thereof is disclosed in EP 168,214, published Jan. 15, 1986 (Genentech) and PCT US85/01921, filed Oct. 3, 1985, published April, 1986 (Cetus Corporation). The latter, PCT 85/01921 corresponds to U.S. Ser. No. 760,661 filed Jul. 30, 1985, the disclosure of which is incorporated herein by reference.

Combination chemotherapy using two or more anticancer drugs to treat malignant tumors in humans is currently in use in research and in the clinic. The anticancer drugs may be antimetabolites, alkylating agents, antibiotics, general poisons, etc. Combinations of drugs are administered in an attempt to obtain a synergistic cytotoxic effect on most cancers, e.g., carcinomas, melanomas, lymphomas and sarcomas, and to reduce or eliminate emergence of drug-resistant cells and to reduce side effects to each drug.

It is known that Type I and Type II interferons may be combined to produce a synergistic biological effect. See, for example, Fleishmann, W. R., *Cancer Res.* (1982), 42:869–875 and DeClercq, E., et al., *Cancer Letters* (1982), 15:223–228 (mouse IFNs), and European Patent Publ. 107,498 published May 2, 1984 (human IFN-$\gamma$ and IFN-$\alpha$ or -$\beta$).

U.S. Pat. No. 4,518,584 to Mark et al. (Cetus Corporation) discloses the combination of IL-2 muteins with gamma-interferon, B cell growth factor, and IL-1. In addition, it has been disclosed that IL-2 may be used with IFN-$\gamma$ to treat tumor-bearing hosts with synergistic results (European Patent Publ. 149,551 published Jul. 24, 1985 (Genentech) and German Patent Publication 3411184 published Oct. 31, 1985 (Deut Roten Kreuzes)) or with augmentation of natural killer activity (Svedersky et al., *J. Immunol.* (1984), 133:714–718 and Shalaby et al., *J. Interferon Res.* (1985), 5:571–581.) Lopez-Botet et al., *Eur. J. Immunol.* (1984), 14:1137–1141 reported, however, that IL-2 and IFN-$\gamma$ are not sufficient in combination to induce natural killer-like activity in human T cell clones. It is also known from Dempsey et al., *J. Immun.* (1982), 129:2504–2510 that the combination of IFN-$\alpha$ and IL-2 is more effective than IFN-$\alpha$ or IL-2 alone in causing natural killer cell activation.

Lymphotoxin and TNF were once thought to be synomymous, but Stone Wolff et al., *J. Exp. Med.*, 159:828–843 (1984) has shown that they are not the same protein. Lymphotoxin has a molecular weight of 60,000–70,000 daltons, whereas TNF has a lower molecular weight. EP 131,789 published Jan. 23, 1985 (Sloan-Kettering) discloses the synergistic effect of lymphotoxin and IFN-$\gamma$ to treat tumors in mice. Williamson et al., *Proc. Natl. Acad. Sci.* (U.S.A.) 50:5397–5401 (1983) discloses the in vivo effects of human lymphotoxin and human IFN. Others have published on the combined activity of lymphotoxin and antitumor drugs or interferons. See Williams et al., *J. Immunol.*, 130:518–520 (1983), Matsunaga et al., *Cancer Letters*, 20:21–28 (1983) and Papermaster et al., *Human Lymphokines*, Khan et al., ed., p. 459–477 (Jun. 30, 1982).

Dr. Talmadge of the Preclinical Screening Lab., BRMP has reported in 1986 the augmented effect of using TNF and IFN-$\gamma$ to treat metastatic disease in mice. U.S. Pat. No. 4,650,674 issued Mar. 17, 1987, filed Dec. 3, 1984 (Genentech) discloses the synergistic effect of TNF and IFN to treat various tumors. EP 170,843, published Jun. 20, 1985 (Boehringer Ingelheim) discloses the synergistic effect of TNF and IFN-$\alpha$, $\beta$ and/or $\gamma$ on cancerous growth, particularly mixtures containing TNF and IFN-$\gamma$. See also matthews et al., *Chem. Abs.* 92:108513h (1980), which discloses injecting rabbits with BCG and endotoxin to induce TNF and IFN in vivo, and Buessow et al., *Leukemia Research*, 8:801–811 (1984), which discloses augmenting the cell-mediated tumoricidal activity of the HL-60 cell line using IFN-$\alpha$.

SUMMARY OF THE INVENTION

Accordingly, the present invention provides a composition suitable for parenteral or subcutaneous administration to mammalian hosts for therapeutic treatment of cancer comprising a mixture of TNF and IL-2 and/or IFN-$\beta$ in synergistically effective amounts, wherein the TNF, IL-2 and IFN-$\beta$ are from mammalian species. This composition preferably is free of cells and free of lymphotoxin as described by Gray et al., *Nature*, 312:721–724 (1984), which has a molecular weight of 60,000–70,000 daltons.

In another aspect, the invention provides a method for therapeutic treatment of cancer in mammalian hosts comprising administering a synergistically effective amount of TNF and IL-2 and/or INF-$\beta$ to the host, wherein the TNF, IL-2 and IFN-$\beta$ are from mammalian species, and wherein if the TNF and IL-2 are administered sequentially, the administration of TNF precedes the administration of IL-2.

Preferably the TNF is rabbit or human TNF, the IL-2 is human IL-2, and the IFN-$\beta$ is human or mouse IFN-$\beta$, and all proteins are recombinant, microbially produced proteins.

The combination of IL-2 and TNF is found to provide a surprising synergism in treating various forms of cancer such as melanomas, leukemia, mastocytoma, lung cancer, mammary adenocarcinoma, and pharyngeal squamous cell carcinoma.

DESCRIPTION OF THE PREFERRED EMBODIMENTS

As used herein, the term "therapeutic" treatment refers to administration to the host of the TNF and IL-2 or TNF and IFN-$\beta$, or TNF, IFN-$\beta$, and IL-2 after the host has contracted cancer, as determined by any means. The treatment is not considered therapeutic if after treatment a tumor appears or an existing tumor burden is not decreased or eliminated. The effect of the dose will diminish with time, with from 5–7 days after the tumor is visible being typically the maximum period in which treatment can be given, depending mainly on the type of tumor and dosage levels.

As used herein, the term "cancer" refers to any neoplastic disorder, including such cellular disorders as, for example, renal cell cancer, Kaposi's sarcoma, chronic leukemia, breast cancer, sarcoma, ovarian carcinoma, rectal cancer, throat cancer, melanoma, colon cancer, bladder cancer, mastocytoma, lung cancer, mammary adenocarcinoma, pharyngeal squamous cell carcinoma, and gastrointestinal or stomach cancer. Preferably, the cancer is leukemia, mastocytoma, melanoma, lymphoma, mammary adenocarcinoma, and pharyngeal squamous cell carcinoma.

As used herein, the term "synergistically effective amount" as applied to IL-2 and TNF refers to the amount of each component of the mixture which is effective for survival of the host and which produces a survival level which does not intersect, in a dose-response plot of the dose of TNF versus dose of IL-2 versus host survival, either the dose TNF axis or the dose IL-2 axis. The same applies to IFN-$\beta$ and TNF. If IFN-$\beta$, IL-2 and TNF are all present, three axes are employed for the three components. The dose response curve used to determine synergy herein is more fully described by Sande et al., p. 1080–1105 in A. Goodman et al., ed., *the Pharmacological Basis of Therapeutics*, MacMillan Publishing Co., Inc., New York (1980). For purposes of synergy, cure is defined as cure of the host after 14 days and after 60 days for all other tumors. The optimum synergistic amounts can be determined, using a 95% confidence limit, by varying factors such as dose level, schedule and response, and using a computer-generated model that generates isobolograms from the dose response curves for various combinations of the IL-2 and TNF, IFN-$\beta$ and TNF, or IL-2, IFN-$\beta$ and TNF. The highest survival rates on the dose response curve correlate with the optimum dosage levels.

As used herein, the term "recombinant" refers to TNF, IL-2, and IFN-$\beta$ produced by recombinant DNA techniques wherein generally the gene coding for the TNF, IFN-$\beta$, or IL-2 is cloned by known recombinant DNA technology. For example, by using the human TNF or IL-2 cDNA or mouse IFN-$\beta$ cDNA as a template, the gene showing complementarity to the human TNF or IL-2 cDNA or mouse IFN-$\beta$ cDNA is inserted into a suitable DNA vector such as a bacterial plasmid, preferably *E. coli* plasmid, to obtain a recombinant plasmid, and the plasmid is used to transform a suitable host. The gene is expressed in the host to produce the recombinant protein. Examples of suitable recombinant plasmids for this purpose include pBR322, pCR1, pMB9 and pSC1. The transformed host may be eucaryotic or procaryotic, preferably a procaryotic host.

As used herein, the term "pharmaceutically acceptable" refers to a carrier medium that does not interfere with the effectiveness of the biological activity of the active ingredients and that is not toxic to the hosts to which it is administered.

The method of this invention involves administering to a mammalian host, preferably a cat, dog or human host, a synergistically effective amount of TNF and IL-2, of TNF and IFN-$\beta$, or of TNF, IL-2 and IFN-$\beta$. The IL-2 and/or IFN-$\beta$ and TNF may be combined in vitro before administration or separately administered to the host. The IFN-$\beta$ and TNF may be administered either simultaneously or by administering one component followed by the other, with any second administration generally within about five-ten, preferably about five, minutes of the first administration. If IL-2 and TNF are employed, they may be administered either simultaneously or by administering TNF followed by IL-2, with any second administration generally after the first administration is completed. Administration of IL-2 before the TNF did not result in synergism, and IL-2 may reduce the sensitivity of the tumor to subsequent TNF treatment.

The administration(s) may take place by any suitable technique, including parenteral administration. Examples of parenteral administration include subcutaneous, intravenous, intraarterial, intramuscular, and intraperitoneal, with intraperitoneal administration(s) being preferred (for convenience) with murine models, and intravenous and subcutaneous being preferred for higher mammals.

The dose and dosage regimen will depend mainly on whether the IL-2, IFN-$\beta$, and TNF are being administered separately or as a mixture, the type of cancer, the patient, and the patient's history. The amount must be effective to achieve a tumor reduction that is synergistic. The doses may be single doses or multiple doses. If multiple doses are employed, as preferred, the frequency of administration will depend, for example, on the type of host and type of cancer, dosage amounts, etc. For some types of cancers or cancer lines, daily administration will be effective, whereas for others, administration every other day or every third day will be effective, but daily administration will be ineffective. The practitioner will be able to ascertain upon routine experimentation which route of administration and frequency of administration are most effective in any particular case.

The dosage amount which appears to be most effective herein is one which results in no tumor appearance or complete regression and is not toxic to the host. This optimum level will depend on many factors, for example, on the type of host and type of cancer, route, schedule of administration, existing tumor burden, the type of IL-2, IFN-$\beta$, and TNF, and the definition of toxicity. Toxicity to the host may be defined by the extent and type of side effects or by the amount of body weight loss or by death after a certain period of time. If body weight loss is the criterion for toxicity, typically a loss of from 10–20% by weight will be tolerated, with greater than 20% loss being considered toxic.

If body weight loss of greater than 20% is considered toxic, if the host is murine, if the route of administration is intraperitoneal via a mixture prepared in vitro and is every day or every other day, the dosage level at each administration of recombinant, microbially produced TNF and IL-2 is preferably about 230–260 $\mu$g TNF per kg host weight (more preferably about 250 $\mu$g), and about 15,000–15 million units IL-2 per kg host weight, where 1000 units is 1 $\mu$g (more preferably 15,600–625,000 units).

If body weight loss of greater than 20% is considered toxic, if the host is a dog (and presumably also if the host is a cat or a human), if the route of administration is intravenous for TNF and subcutaneous for IL-2, and if the schedule of administration is TNF daily for three days followed by IL-2 daily for variable periods, preferably nine days, the dosage level at each administration of recombinant, microbially produced TNF and IL-2 is preferably about 100–1200 $\mu$g TNF/sq. m. of host surface and about 2.4–12 million units IL-2/sq. m. of host surface.

For parenteral administration the IL-2, IFN-$\beta$, and TNF will generally be formulated in a unit dosage injectable form (solution, suspension, emulsion), preferably in a pharmaceutically acceptable carrier medium that is inherently non-toxic and non-therapeutic. Examples of such vehicles include saline, Ringer's solution, dextrose solution, mannitol and normal serum albumin. Non-aqueous vehicles such as fixed oils and ethyl oleate may also be used. The carrier medium may contain minor amounts of additives such as substances that enhance isotonicity and chemical stability, e.g., buffers and preservatives. The IL-2, IFN-$\beta$, and TNF will typically be formulated in such carriers at a concentration of about 0.1 mg/ml to 100 mg/ml of each, preferably 0.2 to 1 mg/ml of each.

Alternatively, the IL-2, IFN-$\beta$, and TNF may be made into a sterile, stable lyophilized formulation in which the purified IL-2, IFN-$\beta$, and TNF are admixed with a water-soluble carrier such as mannitol, which provides bulk, and a sufficient amount of a surfactant such as sodium dodecyl sulfate to ensure the solubility of the recombinant IL-2 or IFN-$\beta$ in water. The formulation is suitable for reconstitution in aqueous injections for parenteral administration and it is stable and well-tolerated in human patients. The IL-2 formulation method is more completely described in U.S. Pat. No. 4,604,377, the disclosure of which is incorporated herein by reference.

In yet another alternative, the mixture of IL-2 and TNF may be administered in an adoptive immunotherapy method, together with isolated, lymphokine-activated lymphocytes in a pharmaceutically acceptable carrier, where the lymphocytes are reactive to tumor when administered with the TNF and IL-2 to humans suffering from the tumor. This method is described more fully in copending U.S. Ser. No. 763,657 entitled "IL-2/Adoptive Immunotherapy" filed Aug. 8, 1985 (NTIS), and by S. Rosenberg et al., *New England Journal of Medicine* (1985), 313:1485–1492, the disclosures of which are incorporated herein by reference. In another alternative, described in S. Rosenberg et al., *Science*, 233:1318–1321 (1986), tumor-infiltrating lymphocytes (TIL) expanded in IL-2 may be adoptively transferred for the therapeutic treatment, particularly in combination with cyclophosphamide. The TIL aproach of Rosenberg et al., the disclosure of which is incorporated herein by reference, may also be used herein.

As mentioned above, the IL-2, IFN-β, and TNF herein may be any IL-2, IFN-β, and TNF prepared from tissue cultures or by recombinant techniques, and from any mammalian source, such as, e.g., mouse, rat, rabbit, primate, pig, and human. Preferably the TNF is derived from rabbit or human sources, more preferably human, the IFN-β is derived from a human or mouse source, and the IL-2 is derived from a human source. More preferably, the IL-2, IFN-β, and TNF are recombinant unglycosylated human IL-2, recombinant human or mouse IFN-β, and recombinant unglycosylated human TNF. The recombinant IL-2 may be obtained as described by Taniguchi et al., Nature, 302:305–310 (1983) and Devos, *Nucleic Acids Research*, 11:4307–4323 (1983) by cloning the native human IL-2 gene and expressing it in transformed microorganisms. It may also be an IL-2 mutein as described in U.S. Pat. No. 4,518,584, in which the cysteine normally occurring at position 125 of the wild-type or native molecule has been replaced by a neutral amino acid such as serine or alanine, or an IL-2 mutein as described in copending U.S. application Ser. No. 810,656 filed Dec. 17, 1985, the disclosure of which is incorporated herein by reference, in which the methionine normally occurring at position 104 or the wild-type or native molecule has been replaced by a neutral amino acid such as alanine.

Preferably, the IL-2 is an unglycosylated protein that is produced by a microorganism that has been transformed with the human cDNA sequence or a modified human cDNA sequence of IL-2 that encodes a protein with an amino acid sequence at least substantially identical to the amino acid sequence of native human IL-2, including the disulfide bond of the cysteines at positions 58 and 105, and has biological activity that is common to native human IL-2. Substantial identity of amino acid sequences means the sequences are identical or differ by one or more amino acid alterations (deletions, additions, substitutions) that do not cause an adverse functional dissimilarity between the synthetic protein and native human IL-2. Examples of IL-2 proteins with such properties include those described by Taniguchi et al., Nature (1983), 302:305–310; Devos, *Nucleic Acids Research* (1983), 11:4307–4323; and by European Patent Publication Nos. 91,539 and 88,195; in U.S. Pat. No. 4,518,584, supra, and in copending U.S. application Ser. No. 810,656 filed Dec. 17, 1985, supra, covering, e.g., IL-$2_{ala104ser125}$. Most preferably, the IL-2 is the des-ala$_1$-IL-$2_{ser125}$ mutein in which the initial terminal alanine is deleted and the cysteine at position 125 is replaced by a serine residue and the IL-2 wherein any combination of up to 5 of the first 5 N-terminal amino acid residues are deleted.

The IL-2 may be produced and purified to clinical purity by the method described and claimed in U.S. Pat. No. 4,569,790, issued Feb. 11, 1986, the disclosure of which is incorporated herein by reference.

In an alternative formulation, described in copending U.S. application Ser. No. 866,459, filed May 21, 1986, the disclosure of which is incorporated herein by reference, the IL-2 may be solubilized, not by a detergent, but by reacting the IL-2 with an activated polymer selected from polyethylene glycol homopolymers and polyoxyethylated polyols such as polyoxyethylated glycerol. The polymer preferably has a molecular weight of from 300 to 100,000 daltons, more preferably 350 to 40,000 daltons. The polymer is activated by conjugation with a coupling agent having terminal groups reactive with both the free amine or thiol groups of the IL-2 and the hydroxyl group of the polymer. Examples of such coupling agents include hydroxynitrobenzene sulfonic ester, cyanuric acid chloride, and N-hydroxysuccinimide. This modification eliminates the necessity for adding detergents to solubilize the IL-2 at physiological pH. The IL-2 is then formulated directly with the water-soluble carrier and buffer as described above, the formulation is lyophilized, and the lyophilized mixture may be reconstituted as described above.

The IFN-β herein may be produced naturally by cells exposed to interferon inducers such as viruses or double-stranded polyribomucleotides, as taught by Metz, *Adv. Drug Res.*, 10:101–156 (1975). IFN-β may also be made by recombinant means such as the method disclosed by EP 28,033 published Jun. 6, 1981. Muteins of IFN-β may also be prepared as described by U.S. Pat. No. 4,588,585 issued May 13, 1986, the disclosure of which is incorporated herein by reference. In particular, one IFN-β mutein is IFN-$β_{ser17}$, which is not glycosylated, lacks the N-terminal methionine, and has the cysteine residue at position 17 of native IFN-β replaced by serine using site-specific mutagenesis. The IFN-β may be produced and purified by the method described in U.S. Ser. No. 843,997 filed Mar. 25, 1986 or in U.S. Pat. No. 4,462,940, the disclosures of which are incorporated herein by reference.

In addition, mouse IFN-β, which is the preferred IFN-β herein, may be produced by known recombinant techniques.

The recombinant human TNF may be obtained as described by Pennica et al., *Nature* (1984), 312:724–729; Yamada et al., *J. Biotechnology* (1985), 3:141–153; Wang et al., *Science* (1985), 228:149–154; EP 155,549 published Sep. 29, 1985; EP 158,286 published Oct. 16, 1985; EP 168,214 published Jan. 15, 1986; and PCT US 85/01921 published April, 1986. The TNF is preferably human unglycosylated TNF having a molecular weight of about 15,000–20,000 daltons on SDS-PAGE. The recombinant rabbit TNF may be obtained as described in EP 146,026 published Jun. 26, 1985 and EP 148,311 published Jul. 17, 1985. Preferably the TNF is a human TNF mutein wherein up to the first eight amino acid residues have been deleted, using the procedure described in U.S. Pat. Nos. 4,677,064 and 4,677,063 issued Jun. 30, 1987, or the TNF is a cysteine-depleted mutein described in copending U.S. Ser. No. 698,939 filed Feb. 7, 1985 and in U.S. Pat. No. 4,518,584 (for IL-2, applicable to TNF).

The various aspects of the invention are further described by the following examples, which are not intended to limit the invention in any manner. In these examples all parts for solids are by weight and all percentages for liquids and gases are by volume, unless otherwise noted, and all temperatures are given in degrees Celsius.

EXAMPLE 1

A. General Treatment

Mice

Female BDF1, C57B1 and Balb/c mice and CD rats (Charles River Breeding Laboratories, Inc., Wilmington, Mass), were employed in the in vivo tests. Mice were weight matched and randomized such that treatment groups (5 or 10) averaged 20 g±3 g. All animals were held for quarantine observation for seven days after arrival, maintained in microisolator cages (Lab Products, Inc.) and fed standard laboratory diets with drinking water ad lib.

IL-2

The recombinant IL-2 employed in this example was des-ala$_1$-IL-2$_{ser125}$ described by Wang et al., Science (1984) 224:1431–1433, the disclosure of which is incorporated herein by reference. The amino acid sequence of this IL-2 differs from the amino acid sequence of native human IL-2 in that it lacks the initial alanine of the native molecule, and the cysteine at position 125 has been changed to serine. Samples of E. coli that produce this IL-2 have been deposited by Cetus Corporation in the American Type Culture Collection, 12301 Parklawn Drive, Rockville, Md., USA on Sept. 26, 1983 under accession number 39,452 and on Mar. 6, 1984 under accession number 39,626 under the provisions of the Budapest Treaty.

The IL-2 was processed and purified as described in the text and FIG. 1 of the copending U.S. Ser. No. 715,152 filed Mar. 21, 1985, the disclosure of which is incorporated herein by reference, except that the oxidation was carried out using copper chloride, as described in U.S. Pat. No. 4,572,798 rather than o-iodosobenzoate. When the IL-2 was recovered from the chromatography step(s) it was lyophilized and resuspended in a neutral aqueous buffer containing the reducing agent (DTT) to keep the IL-2 in a reduced state and a solubilizing agent to keep it in solution. The purity of the recombinant IL-2 after the chromatography step(s) was at least about 95% and the IL-2 contained less than about 0.02 ng/ml endotoxin as determined by the Limulus amebocyte assay.

The purified IL-2 (3–5×10$^6$ units/mg) was produced as a lyophilized powder in sterile vials and reconstituted using sterile phosphate buffered saline within four days prior to use and formulated at a concentration of 0.3 mg/ml with 50 mg/ml mannitol.

In an alternative formulation, the IL-2 was formulated as by reaction with polyethylene glycol which was conjugated using N-hydroxysuccinimide. The conjugated protein was formulated directly in water (hereinafter called IL-2-PEG).

TNF

A mutein of human TNF having the first eight amino acids deleted from the N-terminus was prepared as described in U.S. Pat. No. 4,677,064 and Wang et al., Science (1985) 228:149–153, the disclosures of which are incorporated herein by reference. Briefly, TNF was induced from HL-60 cells and purified and sequenced. Then an intronless sequence encoding human TNF was prepared by producing enriched mRNA, constructing a cDNA library, selecting a probe and probing the library to recover the sequence. Then an ATG start codon was introduced immediately preceding the GTC sequence encoding N-terminal valine of the mature protein by site-directed mutagenesis. Clones were selected and strands ligated into expression vectors to obtain procaryotic expression of the mutein. The mutein was then purified by column purification, recovered in the purification buffer, and produced as a lyophilized powder in sterile vials. Finally, it was reconstituted and suspended using sterile phosphate buffered saline within four days prior to use, and stored, if at all, at 4° C. The TNF contained less than 0.001 to 0.006 ng endotoxin/mg protein depending on production lot.

Cancer Cell Lines

The target cells employed were murine tumors L1210 (leukemia), P388 (leukemia), P815 (mastocytoma), and EL-4 (lymphoma), all obtainable from the American Type Culture Collection, Rockville, Md., and B16 (melanoma), which is a subclone of the Fidler line F10 (melanoma murine line) obtained by passage ten times in vitro and in vivo of the Fidler line, and which is described by Winkelhake et al., Cancer Res. (1979) 39:3058–3064, the disclosure of which is incorporated herein by reference.

All cell lines were passed twice in tissue culture (37° C., 8% $CO_2$ in RPMI 1640 medium with 10% fetal bovine serum, 2 mM L-gln) from frozen stocks just prior to implantation. All tumors and cell lines were negative in tests for mycoplasma and for mouse antiviral-antibody-production.

Subcutaneous Tumor Injections

The tumor cells were harvested from culture suspensions or monolayers. For subcutaneous tumors, the cells (5×10$^5$–10$^6$) were injected in the suprascapular region. For intraperitoneal (ip) tumors, 10$^5$ cells were inoculated into the mice. For the B16W10 melanoma intravenous (pulmonary, iv) metastasis model, the cells were removed from tissue culture plates using trypsin-EDTA, rinsed twice in phosphate buffered saline, and 10$^4$ cells were injected into the lateral tail vein in 0.2 ml volume. If the mice were not treated with any lymphokine, they all died within 20–30 days after inoculation, whether ip, iv., or sq.

Experimental Methods

Groups of five mice per dose were utilized except for the B16W10 iv model, where groups sizes were 10. Animals received tumor challenges on Day 0 unless otherwise stated and all treatments were ip, initiated on the indicated day after tumor challenge and continued once per day for 14 days.

For subcutaneous models, tumors were measured using linear calipers in three orthogonal directions by the same measurer throughout each experiment. While there is inter-individual variability when this technique is applied, repeat measurements performed by the same individual showed less than 5% error. All tumors studied were allowed to grow to volumes of approximately two cubic cm, a which point further measurements were difficult and animals were sacrificed.

For ip tumors, animals were observed daily for survival. As all tumors that were studied are lethal to the mice within approximately 30 days of implant, observations for prolongation of lifetime were performed for at least 60 days.

For iv-administration B16 model, animals were sacrificed 17–21 days after cell inoculations, and lung colonies were counted.

B. Results

1. Table I indicates the results obtained when TNF alone, IL-2 alone, and various mixtures of TNF and IL-2 (prepared in vitro) were administered per kilogram mouse weight intraperitoneally to five female BD2F1 mice per group implanted sq with $2 \times 10^6$ P815 cells, beginning one day after tumor implantation (Day 1), continuing every day for 20 days. The control was injected only with PBS daily for 20 days.

In the table, the "palp." abbreviation refers to palpable tumors.

TABLE I

| Treatment | | Tumor Volume (mm³) | | | |
|---|---|---|---|---|---|
| TNF (μg/kg) | IL-2 (units/kg) | Day 10 | Day 14 | Day 17 | Day 21 |
| 0 | 0 | 2 palp. | 37 3 palp. | 2150 | too large to measure |
| 0 | 39,062 | 3 palp. | all palp. | 2900 | too large to measure |
| 0 | 156,250 | 3 palp. | all palp. | 2005 | too large to measure |
| 0 | 625,000 | 1 palp. | all palp. | 1250 | 5675 |
| 50 | 0 | 3 palp. | all palp. | 3300 | too large |
| 125 | 0 | 1 palp. | 2 palp. | 2 at 1660 (4 palp.) | 2800 |
| 250 | 0 | 0 palp. | 0 palp. | 1 palp. | 1 at 769 |
| 50 | 625,000 | 0 palp. | 2 palp. | 3 at 733 | 2905 |
| 250 | 625,000 | 0 palp. | 0 palp. | 0 palp. | 0 palp. |

The results indicated that the subcutaneous model P815 mastocytoma (which was responsive to 250 μg/kg TNF every day for 14 days ip beginning Day 1 and was unresponsive to up to 10 million units/kg of the same regimen of IL-2) was responsive to a 5-fold lower dose of TNF when the IL-2 was administered concomitantly. In addition, no tumors appeared when the TNF and IL-2 were administered together at 250 μg and 625,000 units/kg, respectively.

2. Table II indicates the results obtained when TNF alone, IL-2 alone, and various mixtures of TNF and IL-2 (prepared in vitro) were administered per kg mouse weight intraperitoneally to 10 female BD2F1 mice ($24\pm3$ g weight) per group implanted sq with $10^6$ L1210 cells, beginning one day after tumor implantation (Day 1), continuing every day for 13 days. The control was injected with PBS daily for 13 days.

TABLE II

| Treatment | | Tumor Volume (mm³) | | | |
|---|---|---|---|---|---|
| TNF (μg/kg) | IL-2 (units/kg) | Day 4 | Day 7 | Day 10 | Day 14 |
| 0 | 0 | 8 palp. | 860 | 3879 | too large |
| 250 | 0 | 2 palp. | 543 | 2505 | 5737 (3 too large) |
| 0 | 39,062 | 7 palp. | 1350 | 4308 | too large |
| 250 | 39,062 | 0 palp. | 0 palp. | 0 palp. | 0 palp. |
| 250 | 19,981 | 0 palp. | 0 palp. | 1 palp. | 1 |

TABLE II-continued

| Treatment | | Tumor Volume (mm³) | | | |
|---|---|---|---|---|---|
| TNF (μg/kg) | IL-2 (units/kg) | Day 4 | Day 7 | Day 10 | Day 14 |
| 250 | 9,990 | 1 + (1?) palp. | 405 | 2200 (2 not palp.) | 3380 (2 not palp.) |
| 0 | 625,000 | 0 palp. | 8 palp. | 478 | 2700 (2 too large) |

The results showed that the L1210 tumor did not respond to 250 μg/kg TNF (the maximal tolerated dose) or up to 5 million units/kg of IL-2 when these agents were administered alone. A dose of either over about 260 μg/kg TNF or 937,500 units/kg IL-2 resulted in a body weight loss of over 20%, indicating toxicity. When administered together, the IL-2 and TNF treatment produced no tumors, except if 250 μg TNF per kg was combined with only 7800 units of IL-2 per kg host weight.

3. Table III indicates the results obtained when TNF alone, IL-2 alone, and various mixtures of TNF and IL-2 (prepared in vitro) were administered per kg mouse weight intraperitoneally to five female BDF1 mice per group implanted sq with $1 \times 10^6$ B16 cells, beginning one day after tumor implantation (Day 1), continuing every day for 14 days. The control was injected with PBS daily for 14 days.

TABLE III

| Treatment | | Tumor Volume (mm³) | | |
|---|---|---|---|---|
| TNF (μg/kg) | IL-2 (units/kg) | Day 10 | Day 14 | Day 20 |
| 0 | 0 | 161 | 612 | too large |
| 250 | 0 | 90 | 277 | too large |
| 250 | 62,500 | 0 | 0 | 0 |
| 250 | 625,000 | 0 | 0 | 0 |
| 0 | 62,500 | 65 | 177 | too large |
| 0 | 312,500 | 27 | 133 | too large |
| 0 | 625,000 | 28 | 81 | too large |

The combination of TNF and IL-2 prevented tumor growth, whereas IL-2 or TNF alone did not prevent it. The murine B16 melanoma is very similar to the human melanoma, and therefore many studies have been done on this cell line. The fact that the TNF and IL-2 combination is effective for B16 cells indicates that it may be effective in treating human melanoma.

It was found that the murine tumors L1210, P388 and B16 were basically refractory to TNF whether the tumors were located intraperitoneally or subcutaneously. A marginal reduction in tumor size was observed with L1210. This refractoriness existed whether the TNF treatments were 1, 5 or 10 days after tumor implantation.

4. This experiment was conducted to help define the optimum schedule for administering the combination of IL-2 and TNF. The most rigorous model with which the tumors did not appear (the latest day after tumor implant for successful therapy) was determined.

In this experiment, L1210 tumor cells were implanted in groups of animals and treatment was initiated either 1, 3, 7, 10 or 14 days afterward.

Table IV indicates the results obtained when a mixture of 250 μg/kg TNF and 39,060 units/kg IL-2 was administered intraperitoneally to five female BDF1 mice per group implanted sq with $5 \times 10^6$ L1210 cells, beginning 1, 3, 7, 10 or 14 days after tumor implantation, continuing every day up to 20 days from initial implantation. The control was injected with PBS daily for 19 days.

TABLE IV

| Group | Initial Treatment Day | Tumor Volume (mm³) | |
|---|---|---|---|
| | | Day 10 | Day 20 |
| 1 | 1 | 0 | 0 |
| 2 | 3 | 0 | 0 |
| 3 | 7 | 249 | too large |
| 4 | 10 | 243 | too large |
| 5 | 14 | 271 | too large |
| PBS control | — | 235 | too large |

Groups 3–5 and the PBS control had palpable tumors on Day 7. The data show that the most rigorous model is either a 3- or 5-day one (tumor growth cannot be prevented if treatment is initiated 7 days after tumor implant).

5. Table V indicates the results obtained when TNF alone, IL-2 alone, and various mixtures of IL-2 and TNF per kg mouse weight were administered intraperitoneally to five female BDF1 mice per group implanted sq with $3 \times 10^6$ P388 leukemia cells, beginning one day after tumor implantation (Day 1), continuing every day for 14 days. The control was injected with PBS daily for 14 days.

TABLE V

| Treatment | | Tumor Volume (mm³) | |
|---|---|---|---|
| TNF (µg/kg) | IL-2 (units/kg) | Day 10 | Day 15 |
| 0 | 0 | 187 | 380 |
| 250 | 0 | 100 | 267 |
| 0 | 62,500 | 114 | 306 |
| 0 | 312,500 | 129 | 321 |
| 0 | 625,000 | 43 | 288 |
| 250 | 625,000 | 113 | 297 |
| 250 | 62,500 | 112 | 297 |

All tumors grew progressively from Day 15 and were too large and irregular to measure by Day 21. Therefore, the daily dose of the combination of TNF and IL-2 did not work in the P388 tumor model.

6. In this experiment, IL-2-PEG was used in place of IL-2 and a dose every other day was administered rather than a daily dose. Table VI indicates the results.

TABLE VI

| Treatment | | | | Tumor Volume (mm³) | |
|---|---|---|---|---|---|
| TNF (µg/kg) | IL-2 (units/kg) | IL-2-PEG (units/kg) | Schedule | Day 9 | Day 15 |
| 0 | 0 | 0 | daily | palpable | 271 |
| 0 | 312,500 | 0 | three times per day | palpable | 330 |
| 250 | 625,000 | 0 | days 1, 3, 7 | 0 | 0 |
| 0 | 0 | 6250 | every other day | palpable | 138 |
| 250 | 0 | 6250 | every other day | 0 | 121 |

The results indicated that the treatment with IL-2 and TNF on days 1, 3 and 7 was most effective, whereas daily treatment was not effective.

7. Table VII indicates the results obtained when a mixture of 12,500 units of IL-2 and 5 µg TNF (prepared in vitro) was administered per kg mouse weight ip to five female BDF1 mice per group implanted sq with $1 \times 10^6$ EL-4 mouse lymphoma cells, beginning one day after tumor implantation (Day 1), continuing every day for 14 days. the control was injected with PBS daily for 14 days.

TABLE VII

| Treatment | Tumor Volume (mm³) | | | |
|---|---|---|---|---|
| | Day 8 | Day 12 | Day 15 | Day 20 |
| EL-4 | 0 | 0 | 0 | 0 |
| Control | palp. | 123 | 464 | 2155 |

The combination of TNF and IL-2 prevented tumor growth of EL-4 lymphoma, whereas the control did not prevent it.

8. Table VIII indicates the results obtained when a mixture of 12,500 units IL-2 and 5 µg TNF (prepared in vitro) was administered per kg mouse weight ip to ten female BDF1 mice per group implanted sq with $1 \times 10^6$ B16 cells, beginning at 1, 3, 5, 7 and 10 days after tumor implantation (Day 1), continuing every day for 20 days.

TABLE VIII

| Group | Initial Reaction Day | Tumor Volume (mm³) | | | |
|---|---|---|---|---|---|
| | | Day 9 | Day 12 | Day 15 | Day 20 |
| 1 | 1 | 0 | 0 | 0 | 0 |
| 2 | 3 | palp. | 56 | 326 | 2283 |
| 3 | 5 | palp. | 39 | 199 | 2459 |
| 4 | 7 | palp. | 92 | 356 | 3195 |
| 5 | 10 | palp. | 86 | 284 | 2719 |

The results indicate that only small tumor burdens are cured when the combination therapy is employed.

9. Table IX indicates the results obtained when a mixture of 12,500 units IL-2 and 5 µg TNF (prepared in vitro) was administered per kg mouse weight ip to five or ten female BDF1 mice per group implanted intraperitoneally (ip) or intravenously (iv) with $1 \times 10^5$ B16 cells, beginning one day after tumor implantation (Day 1), continuing every day for at least 14 days. The controls were injected ip or iv with PBS daily for at least 14 days. After 14 days the animals which were injected iv were sacrificed and their lung colonies counted as black nodules, indicated as metastases per set of lungs.

TABLE IX

| Number of Mice/Group | Group | Tumor Site | Results |
|---|---|---|---|
| 5 | 1 | ip | 5/5 alive at Day 25 |
| 5 | 2 | ip control | 1/5 alive at Day 11 |
| 10 | 3 | iv | No lung metastases at Day 17 |
| 10 | 4 | iv control | 41 ± 13 metastases at Day 17 |

The results indicate that for intravenously implanted tumors there is no artificial pulmonary metastasis. For intraperitoneally implanted tumors there is a significant prolongation of life over the control. Therefore, this experiment indicates that the administration of IL-2 and TNF works with tumor cells located anywhere in the body, not just at subcutaneous locations.

EXAMPLE 2

When the target cells implanted into the mouse host were a methylcholanthrene-induced sarcoma (Meth A) (Balb/c) (obtained as an ascites-passed tumor from Dr. Lloyd Old, Memorial Sloan-Kettering, frozen as stock, and passed at least twice in ascites prior to use), 2/kg mouse weight alone, injected ip daily for several days, caused complete regression of the tumors. However, within 60 days 60 days of implantation the tumors grew back in 80% of the mice. In contrast, when a mixture of 50 µg TNF/kg mouse weight and 15,625 units IL-2/kg mouse weight prepared in vitro was injected into the Meth A mice ip daily for the same number of days, within 60 days after implantation none of the tumors grew back. The same IL-2 and TNF were used as employed in Example 1. The results show that the mixture of TNF and IL-2 gave a complete cure, whereas either component alone gave only a 20% cure in the Meth A regression model, which is generally more sensitive to therapeutics than the models of Example 1.

EXAMPLE 3

The experiments of Examples 1 and 2 were repeated several times (except not using P388) to generate data for between 10 to 50 animals per dose group. The maximum tolerated dose (MTD) was defined in these studies as the maximum amount of lymphokine(s) that could be injected such that no deaths occurred and body weight loss during and for five days after therapy was less than 5%. For TNF this MTD was found to be 250 µg/kg (5 µg/20 g mouse). For IL-2, a maximal soluble dose, 8 mg/ml, was utilized at a volume that maintained 0.1 ml for all therapeutic injections. Thus, IL-2 doses were 500–800 µg/kg (10–16 µg/20 g mouse) administered ip on a daily basis for 14 days.

For purposes of this study, "significant" prolongation of life for ip tumor models is defined as time-to-death of greater than 150% of control (PBS treated) groups. Complete block of tumor take ("cure") is defined in the sq models as no measurable tumors evident for 60 days after initial tumor challenge.

The results show that all animals developed sq tumors in the L1210, P815, B16W10 and El-4 models, while 95% of the animals consistently developed sq Meth-A tumors. When the two lymphokines were evaluated for therapeutic efficacy as single agents, some initial growth inhibition was observed (notably with L1210 and P815) with TNF treatments when therapy was started one day after tumor challenge if TNF was administered at the MTD. A similar marginal effect was seen for some non-Meth-A tumor models (notably P815) when IL-2 was administered as a single agent daily for 14 days-again only when therapy was initiated within a day of tumor implant.

In the Meth-A model, the lymphokines were more dramatically effective, because even a single dose of TNF resulted in regression of tumors that had been allowed up to 10 days to grow before therapy was initiated. Similar results were seen for 7–10 day old Meth-A tumors with high doses of IL-2 therapy. When either TNF or IL-2 was given as a single agent at repeated dosage over the first 14 days to animals bearing tumors only one day old, however, Meth-A tumor growth would be delayed about 30 days after cessation of therapy for a significant number of the animals, but a majority developed tumors by day 45.

The results in non-Meth-A models showed that animals receiving an MTD of TNF simultaneously with an optimal (soluble) dose of IL-2 within 1 day after tumor challenge did not develop tumors. Interestingly, while the IL-2 dose in the combination could be cut back in some cases to 1% of the optimal, the amount of TNF in the mixture could not be reduced more than 50% in order to block tumor "takes."

For a definition of susceptible tumor take periods for the various models using the IL-2+TNF combination, a fixed combination dose (250 µg/kg TNF+500 µ/kg of IL-2) that blocked tumor takes in the majority of models when treatment was initiated on day 1 was utilized and then the amount of time each of the tumor types could be allowed to grow was investigated prior to initiating effective combination therapy. The maximal allowable time for tumor take that still allowed for effective TNF+IL-2 therapy averaged 3–5 days, although for B16W10, therapy had to be initiated on day 1. Conversely for Meth-A, 10 day tumors were truly "curable" and exhibited regression. In each of these models, combination treatments beginning after the optimal tumor take period resulted in tumor growth inhibition but not in cures. Interestingly, growth inhibitory effects were seen only early during week one of the two week treatment period (except, of course, for Meth-A where the regression and growth inhibition lasted much longer) and tumors in animals receiving less than totally efficacious TNF+IL-2 doses grew rapidly to control levels during weeks 2 and 3.

The results of single agent and combination (TNF and IL-2 proteotherapy for intraperitoneal models of the 5 murine tumors was studied. In all cases, treatments were initiated one day after tumor cell inoculations. While the combination of TNF and IL-2 blocked tumor take in the subcutaneous models, there were no similar blockages in the intraperitoneal models when these lymphokines were administered in combination or alone. However, a significant prolongation of life was seen for the peritoneal B16 melanoma, EL-4 lymphoma, and Meth-A tumors when the combination of IL-2 and TNF was administered using the same protocol as that which totally blocked tumor takes in the subcutaneous models.

Finally, combination IL-2 and TNF therapy was compared with single agent adminstration in animals inoculated intravenously with B16W10 melanocytes. Studies similar to those testing tumor cell burden-take period for the subcutaneous tumors were also performed so that the maximum amount of time that could be allowed for tumor growth prior to starting curative therapy could be more clearly defined. Treatments with IL-2 and TNF when administered concomitantly at an optimal dose were synergistic if treatment was initiated one day after tumor implant. When treatment was initiated three days after implant, the number of pulmonary metastases were significantly less than controls, but all animals had tumors.

In conclusion, combination TNF+IL-2 therapeutic synergy was found to (a) require TNF at a maximal tolerated daily dose; whereas the amount of IL-2 in the daily regimen could be cut back as much as 99%, (b) be tied to tumor burden or the amount of time that implanted cells were allowed to take prior to initiating therapy, and this time varied depending on tumor type, and (c) be effective for subcutaneous and pulmonary tumors but not result in blocking the take of intraperitoneal tumors.

The synergistic effects of TNF and IL-2 in these models are most certainly due to a complex set of interactions. In addition to an apparent dependence on the host's tumor burden for successful immunotherapy, synergy between TNF and IL-2 may be explained, without limitation to any one theory, by (a) direct TNF action on tumor cells, (b) an increase in cytolytic cell, IL-2 receptor expression perhaps as an indirect result of TNF action on heterogeneous cell populations (e.g., macrophage), causing the release of other lymphokines (e.g., IL-1 which then affects IL-2 receptor expression), or (c) by direct activation of cytolytic cells by both IL-2 and TNF. It is possible, in fact, that the combination hyperactivates T cells or initiates LAK-Like activities. The effects reported here are most likely due to such effector cell phenomena, as evidenced by the fact that the identical combination of TNF and IL-2 does not block tumor take for these same tumors when grown in nude or NIH-3 (Beige-nude-XID) mice that are CTL and LAK and CTL deficient, respectively.

EXAMPLE 4

In this example the sequence of administration of IL-2 and TNF was evaluated to determine optimum protocol. The following experiments were performed:

A. Meth-A Tumors

1. TNF Followed by IL-2

Using the Meth-A tumor model wherein the tumor was subcutaneous, groups of five Balb/c mice bearing the tumor for seven days (or eleven days in one case of PBS=IL-2) were randomized, ear-notched and then treated (Day 0) with TNF, IL-2, TNF followed by IL-2, PBS, or PBS followed by IL-2. The usual termination of tumor volume, body weight and tumor weight measurements was on Day 14. As noted, some groups in these experiments were held for 43 days to assess the frequency of long-term cures (i.e., where the tumor was completely eradicated). The protocols for the experiments are given below; all agents were delivered intraveneously in 0.2 ml volumes (ku=kilounits).

| Initial Agent | Second Agent |
|---|---|
| TNF (50 μg/kg), every third day, two times | None |
| TNF (50 μg/kg), every third day, two times | IL-2 (5 ku/dose), daily five days a week |
| TNF (50 μg/kg), every third day, two times | IL-2 (20 ku/dose), daily five days a week |
| Phosphate buffered saline (PBS), every third day, two times | IL-2 (5 ku/dose), daily five days a week |
| Phosphate buffered saline, every third day, two times | IL-2 (20 ku/dose), daily five days a week |
| Phosphate buffered saline, daily five days a week | None |
| IL-2 (5 ku/dose), daily five days a week | None |
| IL-2 (20 ku/dose), daily five days a week | None |

The results are shown in Table X, where ΔBW is the ratio of the mean body weight at day 14 to the mean body weight at day 0 within a single group of mice, and where ΔTW is the ratio of the mean tumor volume at day 14 to the mean tumor volume at day 0 within a single group of mice.

TABLE X

| Group | ΔBW | ΔTW | Day 14 Cures | Day 14 Deaths | Day 43 Cures | Day 43 Deaths |
|---|---|---|---|---|---|---|
| TNF (50 μg/kg) | 1.18 | 18.5 | 0/5 | 0/5 | — | — |
| +IL-2 (5 ku) | 1.04 | 2.2 | 0/5 | 0/5 | — | — |
| +IL-2 (20 ku) | 1.01 | 0.5 | 3/5 | 0/5 | 3/3 | 1/5 |
| PBS (Day 7 tumors) | 1.19 | 56.1 | 0/5 | 0/5 | — | — |
| +IL-2 (5 ku) | 1.22 | 44.6 | 0/5 | 0/5 | — | — |

TABLE X-continued

| Group | ΔBW | ΔTW | Day 14 Cures | Day 14 Deaths | Day 43 Cures | Day 43 Deaths |
|---|---|---|---|---|---|---|
| +IL-2 (20 ku) | 1.19 | 49.7 | 0/5 | 0/5 | — | — |
| PBS (Day 11 tumors) | 1.25 | 63.3 | — | — | — | — |
| +IL-2 | 1.36 | 39.9 | — | 1/5 (tumor burden) | — | — |
| +IL-2 | 1.16 | 27.9 | — | — | — | — |
| IL-2 (5 ku) | 1.33 | 42.0 | — | — | — | — |
| IL-2 (20 ku) | 1.18 | 49.1 | — | — | — | — |

In conclusion, the administration of TNF followed by IL-2 significantly enhanced the anti-tumor efficacy as compared to either agent alone, resulting in long-term cures in the group treated with 20 ku/dose IL-2. At doses of 5 and 20 ku/dose IL-2 with either a day 7 or day 11 tumor, IL-2 or TNF alone had little/no effect on efficacy.

2. IL-2 Followed by TNF

Using the Meth-A tumor model wherein the tumor was subcutaneous, groups of five Balb/c mice bearing the tumor for seven days (or eleven days in the case of PBS+IL-2) were randomized, ear-notched, and then treated (Day 0) with TNF, IL-2 followed by PBS, PBS followed by TNF, PBS/SDS, or IL-2 followed by TNF. The termination of tumor volume, tumor weight and body weight measurements was on Day 14. The protocols for these experiments are given below; all agents were delivered intravenously in 0.2 ml volumes (ku=kilounits).

| Initial Agent | Second Agent |
|---|---|
| IL-2 (5 ku/dose), daily five days per week | PBS, every third day, two times |
| IL-2 (20 ku/dose), daily five days per week | PBS, every third day, two times |
| PBS + 0.1% SDS, daily five days per week | TNF (50 μg/kg), every third day, two times |
| IL-2 (5 ku/dose), daily five days per week | TNF (50 μg/kg), every third day, two times |
| IL-2 (20 ku/dose), daily five days per week | TNF (50 μg/kg), every third day, two times |
| PBS, daily five days per week | None |
| SDS (1%), daily five days per week | None |

The results are shown in Table XI, where ΔBW and ΔTW are defined for Table X above.

TABLE XI

| Group | ΔBW | ΔTW | Day 14 Cures | Day 14 Deaths |
|---|---|---|---|---|
| IL-2 (5 ku) + PBS | 1.26 | 59.3 | — | — |
| IL-2 (20 ku) + PBS | 1.19 | 54.7 | — | — |
| IL-2 (5 ku) + TNF (50 μg/kg) | 1.27 | 58.3 | — | — |
| IL-2 (20 ku) + TNF (50 μg/kg) | 1.16 | 9.2 | — | — |
| PBS + TNF (50 μg/kg) | 1.14 | 9.7 | 0/4 | 1/5 |
| SDS (0.1%) | 1.23 | 49.0 | — | — |
| PBS | 1.34 | 65.2 | 0/4 | 1/5 (tumor burden) |

The results indicate that no enhancement in efficacy was observed when IL-2 was administered prior to TNF. Without limitation to any one theory, there was a hint of reduction of the TNF killing when IL-2 was administered first, as if IL-2 modulated the sensitivity of the tumor, or of the host, to TNF so as to render this tumor more resistant to TNF killing.

B. L1210 Model

1. TNF Followed by IL-2

Using the L1210 tumor model described in Example I, groups of five BD2F1 mice implanted sq with $3 \times 10^6$ L1210 cells on Day 0 were treated intraperitoneally on Day 3 with TNF and IL-2 together, TNF followed by IL-2, PBS, or IL-2 followed by TNF. The results are shown in Table XII.

TABLE XII

| Group | Agent(s) and Schedule | Tumor Volume (mm³) | | | | |
|---|---|---|---|---|---|---|
| | | Day 10 | Day 13 | Day 18 | Day 21 | Day 27 |
| 1 | 2.5 μg/kg TNF and 6.5 ku/dose IL-2 daily for 10 days | Palpable | 851 | 1480 | Sacrificed (tumors too large to measure) | — |
| 2 | 5 μg/kg TNF daily for 3 days followed by 12.5 ku/dose IL-2 daily for 5 days | 0 | 0 | 0 | 0 | 0 |
| 3 | 12.5 ku/dose IL-2 daily for 3 days followed by 5 μg/kg TNF daily for 5 days | Palpable | 139 | 1456 | Large tumor burden | Sacrificed |
| 4 | 2.5 μg/kg TNF every third day for 2 injections followed by 200 ku/dose IL-2 daily for 5 days | Palpable | 580 | 1627 | Sacrificed (tumors too large to measure) | — |
| 5 | 2.5 μg/kg TNF every third day for 2 injections followed by 12.5 ku/dose IL-2 daily for 5 days | Palpable | 902 | 2083 | Sacrificed (tumors too large to measure) | — |
| 6 | 200 ku/dose IL-2 daily for 3 days followed by 2.5 μg/kg TNF every third day for 2 injections | Palpable | 1521 | 1460 | Sacrificed (tumors too large to measure) | — |
| 7 | 12.5 ku/dose IL-2 daily for 5 days followed by 2.5 μg/kg TNF every third day for 2 injections | Palpable | 291 | 1838 | Sacrificed (tumors too large to measure) | — |
| 8 | PBS control daily for 10 days | Palpable | 1737 | 2242 | Sacrificed (tumors too large to measure) | — |

At Day 27, and after 60 days, Group 2 still has no evidence of tumor formation in this rigorous tumor model. The difference in results between Groups 1, 2, 4 and 5 indicates that scheduling and dosing as well as sequencing of administration are important in obtaining good response in the L1210 model.

EXAMPLE 5

In this example, the Meth-A tumor model described above was used to test the combination of Poly I/C, a commercially available inducer of Class I interferons, with the TNF mutein described above.

When the combination was administered simultaneously, a synergistic anti-tumor efficacy was observed, and in some cases cures, as compared to either agent alone. In experiments to determine effects of sequence of administration, there was no indication that the sequence of Poly I/C and TNF influenced the synergy observed. Both sequences worked equally well.

These experiments indicate that synergy would be expected using cloned mouse IFN-β and TNF together.

EXAMPLE 6

The combination of TNF and IL-2 administered ip daily for 14 days and in various 14-day sequences has shown efficacy against the B16 subcutaneous tumor. This experiment was designed to test whether the administration of TNF and IL-2 in a "clinical" schedule (e.g., weekends off) shows an equivalent effect. In addition, the combination of IL-2 given intramuscularly (im) and TNF given ip daily for 14 days was tested for efficacy.

In this experiment BDF1 female mice, 5 per group, were injected subcutaneously with $5 \times 10^6$ B16 cells per mouse on day 0. Treatment began on day 1. All injections were given ip except where noted. Tumor measurements were taken on days 10, 14, 21, 28, 35 and 42.

Each group of mice was treated according to the following schedule, with 0.25 mg/kg TNF and 1 mg/kg IL-2 administered each time where noted.

| Group | Schedule |
|---|---|
| 1 | PBS daily |
| 2 | TNF (day 1-3), IL-2 (day 4, 5), IL-2 (day 8-12), repeat next two weeks |
| 3 | TNF (day 1-3), IL-2 (day 4, 5), TNF (day 8-10), IL-2 (day 11, 12) |
| 4 | TNF (day 1-5), IL-2 (day 8-12), rest one week, repeat |
| 5 | TNF (day 1-14, ip) + IL-2 (day 1-14, im) |

The endpoint was taken when the tumor volumes reached greater than 2000 mm³ or when there were no tumors after more than 60 days. The results are shown in Table XIII.

TABLE XIII

| Group | Mean Tumor Volume (mm³)/no. Dead | | | | |
|---|---|---|---|---|---|
| | Day 10 | Day 14 | Day 21 | Day 28 | Day 29 |
| 1 | Not palp./0 | Not palp./0 | 45/0 | Too large to measure/1 | sacrificed |
| 2 | Not palp./1 | Not palp./1 | 22/1 | 1579/1 | sacrificed |
| 3 | Not palp./2 | Not palp./2 | 29/2 | 2575/2 | sacrificed |
| 4 | Not palp./1 | Not palp./1 | 12/1 | 1870/2 | sacrificed |
| 5 | —/5 | | | | |

The results show that none of the TNF/IL-2 dosing schedules mimicking a weekend off used in this study showed any efficacy. It appears that in the B16 subcutaneous tumor model, administrations of either TNF, IL-2 or the combination must occur within a 24 hour period, and for a duration of greater than 7 days to be efficacious.

All of the mice receiving TNF ip and IL-2 im were dead by the eighth dose. In addition, control animals that were given an equal volume of saline im died after nine injections. It appears then that the test group could not tolerate the actual injection and that death was not related to the test material.

EXAMPLE 7

This experiment tested previously efficacious combinations against ten-day tumor burden to determine their effectiveness in a more rigorous model.

In this example BDF1 female mice, 5 per group, were injected subcutaneously with $5 \times 10^6$ B16 cells per mouse on day 0. Treatment began on day 11. All injections were given ip and tumor measurements were taken on days 10, 14, 21 and 28.

Each group of mice was treated according to the following dosage and schedule.

| Group | Schedule/Dose |
|---|---|
| 1 | PBS |
| 2 | TNF (0.25 mg/kg) day 11–13, and IL-2 (1 mg/kg) day 14–24 |
| 3 | TNF (0.25 mg/kg) day 11, 13, 15, 17, 19, 21, 23 and IL-2 (1 mg/kg) day 12, 14, 16, 18, 20, 22, 24 |

The endpoint was taken when the tumor volumes reached greater than 2000 mm$^3$ or when there were no tumors after more than 42 days.

The results are shown in Table XIV.

TABLE XIV

| | Mean Tumor Volume (mm$^3$)/no. Dead | | | | | |
|---|---|---|---|---|---|---|
| Group | Day 10 | Day 14 | Day 21 | Day 28 | Day 35 | Day 42 |
| 1 | Not palp./0 | Palp./0 | 778/0 | Too large to measure/3 | sacrificed | |
| 2 | Not palp./0 | Not palp./0 | Not palp./0 | Not palp./0 | Not palp./0 | Not palp./0 |
| 3 | Not palp./0 | Not palp./0 | 824/0 | 1097/3 | sacrificed | |

The results show that the same dose and sequence schedule of TNF (0.25 mg/kg day 1–3) and IL-2 (1 mg/kg day 4–14) that was efficacious against a 1-day tumor was also effective in the more rigorous 10-day B16 subcutaneous model (Group 2). The alternating TNF and IL-2 schedule (Group 3) was not efficacious.

The same amount of IL-2 and TNF given ip simultaneously daily for the first three days and continued for the next 11 days only worked in mice bearing tumors 1 or 3 days old, not in mice bearing tumors 10 days old (the mixture of IL-2 and TNF after 3 days was not as good as sequential administration). This suggests that the sequence may be better than a mixture.

EXAMPLE 8

A. Experimental design

1. Species: rat, CD strain
2. Duration of the treatment: daily for 14 days
3. Route of administration: I.V.
4. Dose levels excipient control, TNF alone at 50 μg/kg, IL-2 alone at 0.5 or 1.0 mg/kg, TNF/IL-2 combined at 50 μg/kg TNF/0.5 mg/kg IL-2 or 50 μg/kg TNF/1.0 mg/kg IL-2.
5. Number of animals per dose level: 5 males and 5 females.
6. Parameters evaluated:
   Mortality
   Body weights and body weight changes
   Clinical sign observations
   Gross necropsy findings
   Hematology
   Possible histopathologic evaluations B. Results Body weight gain was reduced at both TNF/IL-2 combined groups when compared with TNF or IL-2 alone group. Except for 3 female rats that died after one injection of TNF/IL-2 combined dose level of 50 μg/kg TNF/1.0 mg/kg IL-2, all other study animals survived the 14 daily infections. "Bloody stool/diarrhea" was noted for 2 of 3 animals before they were found dead and all three animals had "fluid-filled G.I. tract" at necropsy. All three animals died of apparent TNF toxicity because "bloody stool/diarrhea" or "fluid-filled G.I. tract" was the typical finding for TNF toxicity in the rat. All animals surviving until 14 days of the study had isolated episodes of "bloody stool/diarrhea" only at day 1 and 2 of the study and they had no signs of either IL-2 or TNF toxicity at necropsy. Elevated leukocyte, neutrophil, lymphocyte, and eosinophil counts were noted in both male and female rats at TNF-IL-2 combined dose level of 50 μg/kg TNF/0.5 mg/kg IL-2 or 50 μg/kg TNF/1.0 mg/kg IL-2. Significant depressed erythrocyte count, hemoglobin concentration, and % hematocrit were also noted in both male and female rats in a dose-related fashion for both TNF/IL-2 combined dose levels.

C. Summary

Based upon the results of this study, the maximum tolerated dose (MTD) was established at 50 μg/kg TNF/0.5 mg/kg IL-2 when combined TNF and IL-2 was administered intravenously to the rat for 14 consecutive days. This MTD was comparable with the MTD when TNF was treated alone and somewhat lower than when IL-2 was treated alone (the MTD for IL-2 alone was at 1.0 mg/kg).

No different toxicity findings were observed when combined TNF and IL-2 were administered under this testing condition when compared to when TNF or IL-2 was given alone. The true "no observable effect level" (NOEL) was not established from the results of this study because of the reduced body weight gain, elevated leukocyte and differential leukocyte counts, and decrease in erythrocyte counts and related parameters.

EXAMPLE 9

Seven dogs were entered in an experimental study to determine the efficacy and toxicity of the sequential use of the same TNF and IL-2 muteins as used in previous examples. The protocol involved the intravenous injection of TNF for three successive days followed by nine days of subcutaneously administered IL-2. After a nine-day rest period, the cycle was repeated. Additional cycles were allowed if any response was obtained. This protocol was used because it was the most efficacious schedule in the mouse tumor models. A detailed description of the course of treatment and the response for each dog are found in Table XV.

Four tumor types, which are spontaneous tumors, were represented in the seven dogs. Four dogs had malignant melanomas, and one dog each had pharyngeal squamous cell carcinoma, mast cell tumor, and mammary adenocarcinoma. All but one dog had failed to respond to conventional therapy.

Malignant melanomas are common neoplasms in the dog, and usually arise in the pigmented tissues of the mouth. They are highly invasive, and metastases throughout the body are common. Melanomas are resistant to all currently known therapies. Mammary tumors are common in the older, non-neutered female, and when malignant, metastases to the lung are common. Early mammary tumors are usually successfully treated surgically, but if they are particularly malignant, regrowth or metastasis is usual, and further treatment is ineffectual. Mast cell tumors are highly invasive and metastatic. Because the tumor is normally widespread throughout the body, surgery or radiation therapy is not practical. The tumor is resistant to most chemotherapeutics.

All four dogs with malignant melanomas showed some degree of positive response. In three of these dogs, the entire visible mass disappeared—either at the end of the first cycle or early in the second cycle. Two of these dogs had eventual regrowth of the tumor, and ultimately died. However, to have any response with this tumor type is remarkable. The third dog, in the middle of the second cycle, shows no evidence of tumor regrowth. In the fourth dog the disease has become stable, with no further growth of the tumor.

The dog with the mast cell tumor died on the last day of the first cycle. At necropsy there was gross evidence of widespread necrosis of both the primary tumor mass and multiple metastases, indicating that some reaction to the drugs was taking place.

Neither the dog with pharyngeal carcinoma nor the dog with mammary adenocarcinoma has shown any reduction in tumor mass through two cycles. Each dog appeared clinically to feel better, and the rate of progression of disease seemed to be diminished.

With these seven dogs, an acceptable dose and schedule for the combined use of TNF and IL-2 has most likely been determined. The responses seen in these dogs were highly encouraging.

TABLE XV

A. Dog - 8 yr neutered female Shepherd Cross
Mast Cell Tumor - large mass in axilla, mast cells seen in bone marrow and peripheral blood
Cycle 1 -
TNF -  100 µg/m$^2$ × 3 days
IL-2 -  3 million u/m$^2$ × 4 days
        (where u = units)
        4.5 million u/m$^2$ × 4 days
        6 million u/m$^2$ × 2 days -   died day 14
Gross necropsy: probable cause of death - perforated duodenal ulcer widespread metastases, all grossly necrotic

B. Dog - 13 yr female Tibetan Terrier
Mammary Adenocarcinoma, pulmonary metastases - previous treatment with oral IFN and IL-2; radiation; adriamycin
Cycle 1 -
TNF -  250 µg/m$^2$ × 3 days
IL-2 -  2.4 million u/m$^2$ × 4 days
        12 million u/m$^2$ × 4 days:   severe toxicity,
        6 million u/m$^2$ × 3 days     no reduction
        3 million u/m$^2$ × 1 day      in tumor mass

TABLE XV-continued

Cycle 2 -
TNF -  100 µg/m$^2$ × 3 days
IL-2 -  3 million u/m$^2$ × 4 days
        4.5 million u/m$^2$ × 4 days   severe diarrhea
        6 million u/m$^2$ × 4 days     and vomiting,
                                       severe cough,
                                       required
                                       supportive care
Dog looks, feels better, but no reduction in tumor size

C. Dog - 7 yr neutered female Queensland Heeler
first diagnosis: pharyngeal papilloma
second diagnosis (3 months later): pharyngeal squamous carcinoma
Previous treatment: oral IFN, IL-2 and cyclophosphamide: minor response
Cycle 1 -
TNF -  125 µg/m$^2$ × 3 days
IL-2 -  6 million u/m$^2$ × 4 days
        12 million u/m$^2$ × 3 days -  stopped, toxicity
Skip 1 day
        6 million u/m$^2$ × 2 days -   stopped, toxicity
Cycle 2 -
TNF -  1000 µg/m$^2$ × 2 days
Skip 1 day
IL-2 -  3 million u/m$^2$ × 4 days
        4.5 million u/m$^2$ × 4 days
        6 million u/m$^2$ × 1 day -    stopped, toxicity
Dog is clinically much improved (eating, barking), but a biopsy 2 weeks after completion of the second cycle revealed no reduction in tumor mass

D. 11 yr male Beagle
Oral malignant melanoma - no prior treatment
Cycle 1 -
TNF -  125 µg/m$^2$ × 3 days:          noticeable
                                        toxicity
IL-2 -  6 million u/m$^2$ × 4 days:    continuing
                                        toxicity
        12 million u/m$^2$ × 4 days:   unacceptable
                                        toxicity
        6 million u/m$^2$ × 4 days
6 day rest - dog returned to normal, no change in tumor
Cycle 2 -
TNF -  1000 µg/m$^2$ × 2 days
1 day rest - entire visible tumor sloughed
IL-2 -  3 million u/m$^2$ × 4 days
        4.5 million u/m$^2$ × 4 days
        6 million u/m$^2$ × 2 days -   stopped,
                                        toxicity; tumor
                                        growing back
8 day rest
Cycle 3 -
TNF -  200 µg/m$^2$ × 1 day       ⎫   no reduction in
TNF -  300 µg/m 2 × 1 day         ⎬   tumor size, but
TNF -  400 µg/m$^2$ × 1 day       ⎭   no new growth
IL-2 -  3 million u/m$^2$ × 4 days
        4.5 million u/m$^2$ × 4 days
        6 million u/m$^2$ × 4 days -   much better
                                        tolerated
6 day rest
Cycle 4
TNF -  500 µg/m$^2$ × 1 day
       700 µg/m$^2$ × 1 day
       900 µg/m$^2$ × 1 day
IL-2 -  3 million u/m$^2$ × 6 days:    Pica, neuro-
                                        logical signs,
                                        weight loss
6 day rest
Cycle 5
TNF -  1000 µg/m$^2$ × 1 day
       1200 µg/m$^2$ × 2 days -        major regrowth
Euthanized; tumor growing, weight loss, dog miserable
Gross necropsy - scattered small lung metastases

E. Dog - 15 yr male Golden Retriever
Oral malignant melanoma, metastasis to submaxillary lymph node
Cycle 1 -
TNF -  100 µg/m$^2$ × 3 days
IL-2 -  3 million u/m$^2$ × 4 days
        4.5 million u/m$^2$ × 1 day -  stopped, toxicity
6 day rest - oral mass disappeared, lymph node necrotic leading to sepsis, treated with antibiotics TABLE XV-continued Cycle 2 -
TNF -   200 μg/m² × 1 day
        500 μg/m² × 1 day
        800 μg/m² × 1 day
IL-2 -  3 million u/m² × 10 days led to necrotic
        node, shock, depression, oral regrowth minimal; died
Gross necropsy - riddled with metastases, most necrotic F. Dog - 9 yr neutered male Spaniel Cross Malignant melanoma, oral cavity - prior treatment: Oral IFN, IL-2, cyclophosphamide
Cycle 1 -
TNF -   100 μg/m² × 3 days
IL-2 -  3 million u/m² × 4 days
        4.5 million u/m² × 4 days
        3 million u/m² × 2 days -    stopped, toxicity -
                                     no reduction
                                     in tumor mass,
                                     but no growth
                                     either
Cycle 2 -
TNF -   200 μg/m² × 1 day
        400 μg/m² × 1 day
        600 μg/m² × 1 day
IL-2 -  3 million u/m² × 9 days:     slight reduction,
                                     some necrosis
Cycle 3 -
TNF -   200 μg/m² × 1 day
        500 μg/m² × 1 day
        800 μg/m² × 1 day:           no change,
                                     no new growth G. 13 yr neutered female German Shepherd Oral malignant melanoma - prior treatment with hyperthermia and intralesional Cis-platinum
Cycle 1 -
TNF -   100 μg/m² × 3 days
IL-2 -  3 million u/m² × 12 days -   entire visible
                                     tumor gone
6 day rest
Cycle 2 -
(20 days
after Cycle
1 start) -
TNF -   200 μg/m² × 1 day -          no new
                                     tumor growth
Plan to go to 500 μg/m² TNF, then 800 μg/m² TNF, followed by 3 million u/m² IL-2 × 12 days In summary, the present invention is seen to provide a combination of TNF and IL-2 and/or IFN-β which has anti-tumor activity and, furthermore, which does not cause significant increased toxicity in mammalian hosts. It is unexpected that TNF, which kills some cells in human tumor models in vitro but not in nude mouse xenograft models of those cells tested in vivo, nor in the classical murine tumor models in vivo, would be an effective anti-cancer agent when combined with small amounts of IL-2 and/or IFN-β. It is also unexpected that the TNF and IL-2 cytokine mixture does not cause significant increases in toxicity (because it is known that the combination of IL-2 and IFN-γ is significantly more toxic than either agent alone).

Modifications of the above-described modes for carrying out the invention which are obvious to those skilled in the fields of molecular and clinical biology, pharmacology, and related fields are intended to be within the scope of the following claims.

What is claimed is:

1. A composition for therapeutic treatment of cancer comprising a mixture of TNF and IL-2 in synergistically effective amounts, wherein the TNF, and IL-2, are from a mammalian species.

2. A composition for therapeutic treatment of cancer in mammalian host, comprising a mixture of TNF and IL-2 in synergistically effective amounts, wherein said TNF and IL-2 are from a mammalian species and said cancer is bladder cancer.

3. The composition of claim 2 further comprising a pharmaceutically acceptable carrier medium for said TNF and IL-2.

4. The composition of claim 2, wherein said TNF is human or rabbit and said IL-2 is human IL-2.

5. The composition of claim 4, wherein said TNF and IL-2 are recombinant, and said TNF is human TNF.

6. The composition of claim 5, wherein said TNF is a mutein with the first eight amino acids deleted and said IL-2 is des-ala$_1$-IL-2$_{ser125}$.

7. The composition of claim 6, wherein said composition consist of 230–260 μg TNF/kg of host weight and that IL-2 is about 15,000–18,000 units IL-2/kg of host weight.

8. The composition of claim 5, wherein IL-2 is attached to polyethylene glycol prior to administration.

9. A method for therapeutic treatment of cancer in mammalian hosts comprising administering a synergistically effective amount of TNF and IL-2, wherein said TNF and IL-2 are from a mammalian species.

10. A method for a therapeutic treatment of cancer in mammalian host comprising administering a synergistically effective amount of TNF and IL-2, wherein said TNF and IL-2 are from a mammalian species and said administration of TNF precedes the administration of IL-2, and said cancer is bladder cancer.

11. The method as described in claim 10, wherein said IL-2 precedes the administration of TNF.

12. The method as described in claim 10, wherein said TNF and IL-2 are employed and are administered separately to the host.

13. The method of claim 10, wherein said TNF and IL-2 are employed and are mixed in vitro prior to administration of said host.

14. The method of claim 10, wherein said TNF and IL-2 are employed and said TNF is human or rabbit TNF and said IL-2 is human IL-2.

15. The method of claim 14, wherein said TNF and IL-2 are recombinant and said TNF is human TNF.

16. The method of claim 15, wherein said TNF and IL-2 are microbially produced and are administered parenterally.

17. The method of claim 16, wherein said TNF is a mutein with the first eight amino acids deleted, and said IL-2 is des-ala$_1$-IL-2$_{ser125}$.

18. The method of claim 17, wherein said TNF comprises about 100–1200 μg TNF per square meter of host surface and said amount of IL-2 is about 2.4–12 million units IL-2 per square meter of host surface.

19. The method of claim 18, wherein said TNF is administered daily for three days and said IL-2 is then administered daily for nine days.

20. The method of claim 19, wherein said TNF is administered intravenously and said IL-2 is administered subcutaneously.

21. The method of claim 20, wherein said host is a dog, cat, or a human.

22. The method of claim 20, wherein said host is human.

23. The method of claim 16, wherein said IL-2 is conjugated to polyethylene glycol prior to administration.

24. The method of claim 10, wherein said TNF and IL-2 are admixture with a pharmaceutically acceptable carrier medium prior to administration.

* * * * *